US007169590B2

(12) United States Patent
Ueda et al.

(10) Patent No.: US 7,169,590 B2
(45) Date of Patent: Jan. 30, 2007

(54) METHOD OF STABILIZING REDUCED COENZYME $Q_{10}$ AND METHOD OF ACIDIC CRYSTALLIZATION

(75) Inventors: Takahiro Ueda, Hyogo (JP); Shiro Kitamura, Hyogo (JP); Yasuyoshi Ueda, Hyogo (JP)

(73) Assignee: Kaneka Corporation, Osaka (JP)

( * ) Notice: Subject to any disclaimer, the term of this patent is extended or adjusted under 35 U.S.C. 154(b) by 74 days.

(21) Appl. No.: 10/484,227

(22) PCT Filed: Jul. 15, 2002

(86) PCT No.: PCT/JP02/07148

§ 371 (c)(1),
(2), (4) Date: May 10, 2004

(87) PCT Pub. No.: WO03/008363

PCT Pub. Date: Jan. 30, 2003

(65) Prior Publication Data

US 2004/0197418 A1    Oct. 7, 2004

(30) Foreign Application Priority Data

Jul. 16, 2001  (JP) ............................. 2001-215804
Apr. 17, 2002  (JP) ............................. 2002-114878

(51) Int. Cl.
*C12N 9/96* (2006.01)

(52) U.S. Cl. ...................... 435/188; 549/409; 424/94.3

(58) Field of Classification Search ................ 435/188; 549/409; 424/94.3
See application file for complete search history.

(56) References Cited

U.S. PATENT DOCUMENTS 3,658,648 A * 4/1972 Nakao et al. ............... 435/133

6,184,255 B1 * 2/2001 Mae et al. ................... 514/720

FOREIGN PATENT DOCUMENTS

| JP | 52-72884 A | | 6/1977 |
| JP | 53-133687 A | | 11/1978 |
| JP | 56140947 A | * | 11/1981 |
| JP | 10-109933 | | 4/1998 |
| JP | 10-509732 A | | 9/1998 |
| WO | WO 96/17626 A2 | | 6/1996 |
| WO | WO 01/52822 A1 | | 7/2001 |

OTHER PUBLICATIONS

International Search Report From Corresponding PCT Application No. PCT/JP02/07148, Dated Oct. 21, 2002, 1 Page.
Patent Cooperation Treaty International Preliminary Examination Report (PCT Article 36 and Rule 70), From Corresponding International Application No. PCT/JP02/07148, Dated Feb. 27, 2003, 3 Pages.

* cited by examiner

*Primary Examiner*—Leon B. Lankford, Jr.
*Assistant Examiner*—Susan E. Fernandez
(74) *Attorney, Agent, or Firm*—Brinks Hofer Gilson & Lione

(57) ABSTRACT

The present invention relates to a method of efficiently producing reduced coenzyme $Q_{10}$ having excellent qualities which is useful as an ingredient in foods, functional nutritive foods, specific health foods, nutritional supplements, nutrients, animal drugs, drinks, feeds, cosmetics, medicines, remedies, preventive drugs, etc. This method is suitable for industrial production thereof.

It is possible to handle reduced coenzyme $Q_{10}$ in state of being protected from oxidation by molecular oxygen by bringing the reduced coenzyme $Q_{10}$ in contact with a solvent containing a strong acid. Furthermore, when reduced coenzyme $Q_{10}$ is crystallized in the presence of a strong acid, crystallization can be carried out while the formation of oxidized coenzyme $Q_{10}$ as a by product is minimized, and, then high-quality crystals thereof can be produced.

29 Claims, No Drawings

METHOD OF STABILIZING REDUCED COENZYME $Q_{10}$ AND METHOD OF ACIDIC CRYSTALLIZATION

RELATED APPLICATIONS

This application is a nationalization of PCT Application No. PCT/JP02/07148 filed Jul. 15, 2002. This application claims priority from Japanese Patent Application No. 2001-215804 filed on Jul. 16, 2001 and Japanese Patent Application No. 2002-114878 filed on Apr. 17, 2002.

TECHNICAL FIELD

The present invention relates to a method of stabilizing and a method of crystallizing reduced coenzyme $Q_{10}$. Reduced coenzyme $Q_{10}$ shows a higher level of oral absorbability as compared with oxidized coenzyme $Q_{10}$ and is a compound useful as an ingredient in good foods, functional nutritive foods, specific health foods, nutritional supplements, nutrients, animal drugs, drinks, feeds, cosmetics, medicines, remedies, preventive drugs, etc.

BACKGROUND ART

It is known that reduced coenzyme $Q_{10}$ can be prepared by producing coenzyme $Q_{10}$ in the conventional manner, for example by synthesis, fermentation, or extraction from natural products, and concentrating a reduced coenzyme $Q_{10}$-containing eluate fraction resulting from chromatography (JP-Hei-10-109933-A) On that occasion, as described in the above-cited publication, the chromatographic concentration may be carried out after reduction of oxidized coenzyme $Q_{10}$ contained in the reduced coenzyme $Q_{10}$ with a conventional reducing agent such as sodium borohydride or sodium dithionite (sodium hyposulfite), or reduced coenzyme $Q_{10}$ may be prepared by reacting the reducing agent mentioned above with an existing highly pure grade of coenzyme $Q_{10}$.

However, the thus-obtained reduced coenzyme $Q_{10}$ cannot always be in a highly pure state but tends to occur as a low-purity crystalline, semisolid, or oily product containing such impurities as oxidized coenzyme $Q_{10}$. Thus, even if a reaction product of reduced coenzyme $Q_{10}$ containing no or few oxidized coenzymes $Q_{10}$ is obtained in a reduction reaction, it is very difficult to obtain a high-quality reduced coenzyme $Q_{10}$ crystalline.

And, reduced coenzyme $Q_{10}$ is readily oxidized to oxidized coenzyme $Q_{10}$ by molecular oxygen. On a commercial production scale, complete oxygen elimination is very difficult to achieve and, furthermore, fairly long periods of time are required for individual operations, unlike laboratory scale production, so that residual oxygen exerts a great adverse effect. The oxidation in question is directly connected with such yield and quality problems as the formation of hardly eliminable oxidized coenzyme $Q_{10}$ and adulteration of the product therewith.

Thus, it is a very important task to stabilize reduced coenzyme $Q_{10}$, namely to protect the same against oxidation. Up to the present, however, no commercial grade of reduced coenzyme $Q_{10}$ has been on the market, so that how to preserve reduced coenzyme $Q_{10}$ stably, for instance, has been scarcely made. Only there is found WO 01/52822 A1 describing the use of a reducing agent in a method of stabilization and in a composition.

SUMMARY OF THE INVENTION

In view of the foregoing, it is an object of the present invention to provide a simple and easy method of stabilizing reduced coenzyme $Q_{10}$ and a simple and easy and efficient method of crystallization for obtaining high-quality reduced coenzyme $Q_{10}$.

The present inventors made intensive investigations to accomplish the above objects and, as a result, found that reduced coenzyme $Q_{10}$ is very markedly stabilized in the presence of a small amount of a strong acid against oxidation by molecular oxygen and, further, that when reduced coenzyme $Q_{10}$ is crystallized in the presence of a strong acid, high-quality crystals thereof can be obtained while the formation of oxidized coenzyme $Q_{10}$ as a by product is minimized. Such findings have led to completion of the present invention.

Thus, the invention provides a method of stabilizing reduced coenzyme $Q_{10}$ which comprises handling reduced coenzyme $Q_{10}$ in contact with a solvent containing a strong acid to thereby protect reduced coenzyme $Q_{10}$ against oxidation by molecular oxygen. The invention also provides a method of crystallizing reduced coenzyme $Q_{10}$ which comprises crystallizing reduced coenzyme $Q_{10}$ in a solvent containing a strong acid.

DETAILED DISCLOSURE OF THE INVENTION

In the following, the present invention is described in detail.

In accordance with the invention, a strong acid is used for obtaining high-quality reduced coenzyme $Q_{10}$ crystals or stably handling reduced coenzyme $Q_{10}$ while inhibiting the oxidation, by molecular oxygen, of reduced coenzyme $Q_{10}$ to oxidized coenzyme $Q_{10}$.

The strong acid is not particularly restricted but, for example, it is preferably one showing, in aqueous solution, a pKa value of not more than 2.5, more preferably not more than 2.0, still more preferably not more than 1.5, most preferably not more than 1.0. When the strong acid is a polybasic acid, such as sulfuric acid, the pKa value refers to the value in the first stage of dissociation where the value becomes smallest.

As specific examples of the strong acid, there may be mentioned inorganic acids such as sulfuric acid, hydrogen chloride (including hydrochloric acid), and phosphoric acid; and organic acids such as methanesulfonic acid, ethanesulfonic acid, benzenesulfonic acid, p-toluenesulfonic acid, like sulfonic acids, trifluoroacetic acid, trichloroacetic acid and like carboxylic acids, etc. Among them, such inorganic acids as sulfuric acid, hydrogen chloride, and phosphoric acid are preferred and, from the viewpoint of evaporability of the strong acid after crystallization, which is to be mentioned later herein, hydrogen chloride is most preferred.

The amount of the strong acid to be used may depend on the strong acid species but, generally, a catalytic amount or a larger amount will be sufficient. Thus, the amount is preferably not smaller than 0.1 mol %, more preferably not smaller than 1 mol %, per mole of reduced coenzyme $Q_{10}$. The upper limit is not particularly restricted but, from the economical viewpoint, among others, it is preferably not more than 1000 mol %, more preferably not more than 100 mol %.

When reduced coenzyme $Q_{10}$ is handled in contact with a solvent containing a strong acid in accordance with the invention, it is protected against oxidation by molecular oxygen and, when reduced coenzyme $Q_{10}$ is crystallized from a solvent containing a strong acid, high-quality reduced coenzyme $Q_{10}$ crystals can be obtained.

The strong acid concentration in the solvent may vary depending on the strong acid species, hence is not particularly restricted. Preferably, it is not lower than 0.1 mmol/kg, more preferably not lower than 1 mmol/kg, as expressed in terms of the molar amount quantity of the strong acid relative to solvent weight. The upper limit is not particularly restricted but, from the economical viewpoint and so forth, it is preferably 100 mmol/kg. After accomplishment of its purpose of protection against oxidation, the strong acid may be removed, for example, by neutralization, evaporation, phase separation, or washing according to need in some instances. In view of this, it is of course preferable that the strong acid be used in a necessary and minimum amount based on the purpose of use and the obtainable effect.

In bringing reduced coenzyme $Q_{10}$ into contact with a strong acid-containing solvent or crystallizing reduced coenzyme $Q_{10}$ in a strong acid-containing solvent, the system may be either homogeneous or heterogeneous. As typical examples of the above system, there may be mentioned a homogeneous liquid phase composed of reduced coenzyme $Q_{10}$, strong acid and solvent; a heterogeneous liquid system consisting of an organic solvent phase containing reduced coenzyme $Q_{10}$ and a strong acid-containing aqueous phase; and a heterogeneous liquid phase consisting of an oily reduced coenzyme $Q_{10}$ phase and a strong acid-containing aqueous phase. Of course, a system highly efficient in contacting between reduced coenzyme $Q_{10}$ and strong acid is more suited for protection against oxidation.

The solvent to be used in the practice of the invention is not particularly restricted but includes hydrocarbons, fatty acid esters, ethers, alcohols, fatty acids, ketones, nitrogen compounds (including nitriles, amides, etc.), sulfur compounds, water, etc.

The hydrocarbons are not particularly restricted, but there may be mentioned, for example, aliphatic hydrocarbons, aromatic hydrocarbons, halogenated hydrocarbons, etc. Preferred are aliphatic hydrocarbons and aromatic hydrocarbons, and more preferred are aliphatic hydrocarbons.

The aliphatic hydrocarbons are not particularly restricted, and may be cyclic or acyclic, or saturated or unsaturated. However, generally they contain 3 to 20 carbon atoms, and preferably 5 to 12 carbon atoms. From the viewpoint of crystallization yield, acyclic aliphatic hydrocarbons are more preferred.

As specific examples, there may be mentioned, for example, propane, butane, isobutane, pentane, 2-methylbutane, cyclopentane, 2-pentene, hexane, 2-methylpentane, 2,2-dimethylbutane, 2,3-dimethylbutane, methylcyclopentane, cyclohexane, 1-hexene, cyclohexene, heptane, 2-methylhexane, 3-methylhexane, 2,3-dimethylpentane, 2,4-dimethylpentane, methylcyclohexane, 1-heptene, octane, 2,2,3-trimethylpentane, isooctane, ethylcyclohexane, 1-octene, nonane, 2,2,5-trimethylhexane, 1-nonene, decane, 1-decene, p-menthane, undecane, dodecane, etc.

Among them, saturated aliphatic hydrocarbons having 5 to 8 carbon atoms are more preferred, and preferably used are pentane, 2-methylbutane and cyclopentane, which have 5 carbon atoms (referred to as "pentanes"); hexane, 2-methylpentane, 2,2-dimethylbutane, 2,3-dimethylbutane, methylcyclopentane, cyclohexane, which have 6 carbon atoms (referred to as "hexanes"); heptane, 2-methylhexane, 3-methylhexane, 2,3-dimethylpentane, 2,4-dimethylpentane, methylcyclohexane, which have 7 carbon atoms (referred to as "heptanes"); octane, 2,2,3-trimethylpentane, isooctane, ethylcyclohexane, which have 8 carbon atoms (referred to as octanes); and a mixture of these. In particular, the above heptanes are particularly preferred since they have a tendency to show a very high effect to protect reduced coenzyme $Q_{10}$ against oxidization, and heptane is most preferred in the viewpoint of crystallization yield.

The aromatic hydrocarbons are not particularly restricted, but generally they contain 6 to 20 carbon atoms, preferably 6 to 12 carbon atoms, and more preferably 7 to 10 carbon atoms. As specific examples, there may be mentioned, for example, benzene, toluene, xylene, o-xylene, m-xylene, p-xylene, ethylbenzene, cumene, mesitylene, tetralin, butylbenzene, p-cymene, cyclohexylbenzene, diethylbenzene, pentylbenzene, dipentylbenzene, dodecylbenzene, styrene, etc. Preferred are toluene, xylene, o-xylene, m-xylene, p-xylene, ethylbenzene, cumene, mesitylene, tetralin, butylbenzene, p-cymene, cyclohexylbenzene, diethylbenzene and pentylbenzene. More preferred are toluene, xylene, o-xylene, m-xylene, p-xylene, cumene and tetralin, and most preferred is cumene.

The halogenated hydrocarbons are not particularly restricted, and may be cyclic or acyclic, or saturated or unsaturated. However, acyclic halogenated hydrocarbons are preferably used in general. Usually, more preferred are chlorinated hydrocarbons and fluorinated hydrocarbons, and chlorinated hydrocarbons are still more preferred. Additionally, ones containing 1 to 6 carbon atoms, preferably 1 to 4 carbon atoms, and more preferably 1 to 2 carbon atoms are used.

As specific examples, for example, there may be mentioned dichloromethane, chloroform, carbon tetrachloride, 1,1-dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane, hexachloroethane, 1,1-dichloroethylene, 1,2-dichloroethylene, trichloroethylene, tetrachloroethylene, 1,2-dichloropropane, 1,2,3-trichloropropane, chlorobenzene, 1,1,1,2-tetrafluoroethane, etc.

Preferred are dichloromethane, chloroform, carbon tetrachloride, 1,1-dichloroethane, 1,2-dichloroethane, 1,1,1-trichloroethane, 1,1,2-trichloroethane, 1,1-dichloroethylene, 1,2-dichloroethylene, trichloroethylene, chlorobenzene and 1,1,1,2-tetrafluoroethane. More preferred are dichloromethane, chloroform, 1,2-dichloroethylene, trichloroethylene, chlorobenzene and 1,1,1,2-tetrafluoroethane.

The fatty acid esters are not particularly restricted, but there maybe mentioned, for example, propionates, acetates, formates, etc. Preferred are acetates and formates, and more preferred are acetates. Ester functional groups thereof are not particularly restricted, but, in general, preferred are alkyl groups or aralkyl groups having 1 to 8 carbon atoms, more preferred alkyl groups having 1 to 6 carbon atoms, and further more preferred alkyl groups having 1 to 4 carbon atoms.

As the propionates, there may be mentioned, for example, methyl propionate, ethyl propionate, butyl propionate, isopentyl propionate, etc.

As the acetates, there may be mentioned, for example, methyl acetate, ethyl acetate, propyl acetate, isopropyl acetate, butyl acetate, isobutyl acetate, sec-butyl acetate, pentyl acetate, isopentyl acetate, sec-hexyl acetate, cyclohexyl acetate, benzyl acetate, etc. Preferred are methyl acetate, ethyl acetate, propyl acetate, isopropyl acetate, butyl acetate, isobutyl acetate, sec-butyl acetate, pentyl acetate, isopentyl acetate, sec-hexyl acetate and cyclohexyl acetate. More preferred are methyl acetate, ethyl acetate, propyl acetate, isopropyl acetate, butyl acetate and isobutyl acetate. Most preferred is ethyl acetate.

As the formates, there may be mentioned, for example, methyl formate, ethyl formate, propyl formate, isopropyl formate, butyl formate, isobutyl formate, sec-butyl formate, pentyl formate, etc. Preferred are methyl formate, ethyl formate, propyl formate, butyl formate, isobutyl formate and pentyl formate, and most preferred is ethyl formate.

The ethers are not particularly restricted, and may be cyclic or acyclic, or saturated or unsaturated. But saturated ones are preferably used in general. Generally, ones containing 3 to 20 carbon atoms, and preferably 4 to 12 carbon atoms and more preferably 4 to 8 carbon atoms are used.

As specific examples, there may be mentioned, for example, diethyl ether, methyl tert-butyl ether, dipropyl ether, diisopropyl ether, dibutyl ether, dihexyl ether, ethyl vinyl ether, butyl vinyl ether, anisol, phenetole, butyl phenyl ether, methoxytoluene, dioxane, furan, 2-methylfuran, tetrahydrofuran, tetrahydropyran, ethylene glycol dimethyl ether, ethylene glycol diethyl ether, ethylene glycol dibutyl ether, ethylene glycol monomethyl ether, ethylene glycol monoethyl ether, ethylene glycol monobutyl ether, etc.

Preferred are diethyl ether, methyl tert-butyl ether, dipropyl ether, diisopropyl ether, dibutyl ether, dihexyl ether, anisol, phenetole, butyl phenyl ether, methoxytoluene, dioxane, 2-methylfuran, tetrahydrofuran, tetrahydropyran, ethylene glycol dimethyl ether, ethylene glycol diethyl ether, ethylene glycol dibutyl ether, ethylene glycol monomethyl ether and ethylene glycol monoethyl ether. More preferred are diethyl ether, methyl tert-butyl ether, anisol, dioxane, tetrahydrofuran, ethylene glycol monomethyl ether and ethylene glycol mono ethyl ether. Still more preferred are diethyl ether, methyl tert-butyl ether, anisol, etc., and most preferred is methyl tert-butyl ether.

The alcohols are not particularly restricted but may be cyclic or acyclic, or saturated or unsaturated. Saturated ones are generally preferred, however. Generally, preferred are monohydric alcohols containing 1 to 20 carbon atoms, more preferred 1 to 12 carbon atoms, further more preferred 1 to 6 carbon atoms, still more preferred 1 to 5 carbon atoms. Dihydric alcohols containing 2 to 5 carbon atoms, and the trihydric alcohol containing 3 carbon atoms are preferred.

As the monohydric alcohol, there may be mentioned, for example, methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 1-decanol, 1-undecanol, 1-dodecanol, allyl alcohol, propargyl alcohol, benzyl alcohol, cyclohexanol, 1-methylcyclohexanol, 2-methylcyclohexanol, 3-methylcyclohexanol, 4-methylcyclohexanol, etc.

Preferred are methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol and cyclohexanol. More preferred are methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol and neopentyl alcohol. Still more preferred are methanol, ethanol, 1-propanol, 2-propanol, 1-butanol, 2-butanol, isobutyl alcohol, 2-methyl-1-butanol and isopentyl alcohol. Most preferred is ethanol.

As the dihydric alcohol, there may be mentioned, for example, 1,2-ethanediol, 1,2-propandiol, 1,3-propandiol, 1,2-butanediol, 1,3-butanediol, 1,4-butanediol, 2,3-butanediol, 1,5-pentanediol, etc. Preferred are 1,2-ethanediol, 1,2-propandiol and 1,3-propandiol, and most preferred is 1,2-ethanediol.

As the trihydric alcohol, glycerol, etc. may be preferably used, for example.

As fatty acids, there may be mentioned, for example, formic acid, acetic acid, propionic acid, etc. Preferred are formic acid and acetic acid, and most preferred is acetic acid.

The ketones are not particularly restricted, and ones having 3 to 6 carbon atoms are preferably used in general. As specific examples, there maybe mentioned, for example, acetone, methyl ethyl ketone, methyl butyl ketone, methyl isobutyl ketone, etc. Preferred are acetone and methyl ethyl ketone, and most preferred is acetone.

The nitriles are not particularly restricted, and may be cyclic or acyclic, or saturated or unsaturated. However, saturated ones are preferably used in general. Generally, ones containing 2 to 20 carbon atoms, preferably 2 to 12 carbon atoms, and more preferably 2 to 8 carbon atoms are used.

As specific examples, there may be mentioned, for example, acetonitrile, propiononitrile, malononitrile, butyronitrile, isobutyronitrile, succinonitrile, valeronitrile, glutaronitrile, hexanenitrile, heptylcyanide, octylcyanide, undecanenitrile, dodecanenitrile, tridecanenitrile, pentadecanenitrile, stearonitrile, chloroacetonitrile, bromoacetonitrile, chloropropiononitrile, bromopropiononitrile, methoxyacetonitrile, methyl cyanoacetate, ethyl cyanoacetate, tolunitrile, benzonitrile, chlorobenzonitrile, bromobenzonitrile, cyanobenzoic acid, nitrobenzonitrile, anisonitrile, phthalonitrile, bromotolunitrile, methyl cyanobenzoate, methoxybenzonitrile, acetylbenzonitrile, naphthonitrile, biphenylcarbonitrile, phenylpropiononitrile, phenylbutyronitrile, methylphenylacetonitrile, diphenylacetonitrile, naphthylacetonitrile, nitrophenylacetonitrile, chlorobenzylcyanide, cyclopropanecarbonitrile, cyclohexanecarbonitrile, cycloheptanecarbonitrile, phenylcyclohexanecarbonitrile, tolylcyclohexanecarbonitrile, etc.

Preferred are acetonitrile, propiononitrile, succinonitrile, butyronitrile, isobutyronitrile, valeronitrile, methyl cyanoacetate, ethyl cyanoacetate, benzonitrile, tolunitrile and chloropropiononitrile. More preferred are acetonitrile, propiononitrile, butyronitrile and isobutyronitrile, and most preferred is acetonitrile.

As the nitrogen compounds other than nitriles, there may be mentioned, for example, nitromethane, acetonitrile, triethylamine, pyridine, formamide, N-methylformamide, N,N-dimethylformamide, N,N-dimethylacetoamide, N-methylpyrrolidone, etc.

As the sulfur compounds, there may be mentioned, for example, dimethyl sulfoxide, sulfolane, etc.

Among the above solvents, alcohols, ketones, nitrogen compounds (including nitriles, amides), and water are preferably used, and alcohols containing 1 to 3 carbon atoms, acetone, acetonitrile and water are more preferred. When ethanol or a mixed solvent composed of ethanol and water is used, the effects of the invention can be maximized.

When a mixed solvent composed of ethanol and water is used, the proportion between ethanol and water is preferably such that ethanol amounts to be not less than 80 w/w %, more preferably not less than 90 w/w %, still more preferably not less than 91 w/w %, still further more preferably not less than 92 w/w %, most preferably not less than 93 w/w %, relative to the sum of ethanol and water. The upper limit is preferably 99.5 w/w %, more preferably 99 w/w %, still more preferably 98 w/w %, most preferably 97 w/w %. Generally, an ethanol proportion of 90 to 99.5 w/w % is suited, and 93 to 97 w/w % is more suited, for practicing the invention.

The concentration of reduced coenzyme $Q_{10}$ in the solvent is not particularly restricted. Since a higher concentration solution tends to be more resistant to oxidation, however, it is more effective to carry out the handling or crystallization preferably at a concentration, expressed as the weight of reduced coenzyme $Q_{10}$ relative to the solvent weight, of not less than 1 w/w %, more preferably not less than 2 w/w %. The upper limit is not particularly restricted but, from the practical operability viewpoint, it is preferably 400 w/w %, more preferably 200 w/w %, still more preferably 100 w/w %, most preferably 50 w/w %.

The operation of handling reduced coenzyme $Q_{10}$ in the practice of the invention is not particularly restricted but includes, among others, extraction, washing with water, concentration, column chromatography, etc, and reduced coenzyme $Q_{10}$ can be favorably protected against oxidation in such operations.

The method of crystallization according to the invention is now described.

The solvent to be used for crystallization may be any of those mentioned hereinabove. As described hereinabove, alcohols, ketones, nitrogen compounds (including nitrites, amides), and water are preferred. Preferred specific species are alcohols containing 1 to 3 carbon atoms such as ethanol, acetone, acetonitrile, and water. Most preferred is ethanol or a mixed solvent composed of ethanol and water.

When an alcohol and/or a ketone is used in the presence of a small amount of water, not only the above-mentioned stabilization is attained but also the solubility of reduced coenzyme $Q_{10}$ is favorably reduced to give a high yield and, in addition, the slurry properties are improved and, in particular, it is worthy of notice that the solid-liquid separability (filterability) can also be improved remarkably.

The proportion between water and the alcohol and/or ketone may vary depending on the solvent species, hence cannot be absolutely specified. Preferably, however, it is such that the sum of the alcohol and ketone accounts for not less than 90 w/w %, more preferably not less than 91 w/w %, still more preferably not less than 92 w/w %, most preferably not less than 93 w/w %, relative to the sum of water and the alcohol and ketone. The upper limit is preferably 99.5 w/w %, more preferably 99 w/w %, still more preferably 98 w/w %, most preferably 97 w/w %. Generally, the invention can be practiced in a proportion, on such basis, of 90 to 99.5 w/w %, most preferably 93 to 97 w/w %.

The crystallization of the reduced coenzyme $Q_{10}$ of the invention can be carried out by utilizing, singly or in combination, a conventional crystallization method such as the cooling crystallization, concentration crystallization, solvent substitution crystallization and crystallization using a poor solvent. In particular, the cooling method (the cooling crystallization method), or a combination of the cooling method with some other method of crystallization is preferred.

In crystallizing reduced coenzyme $Q_{10}$ of the invention, it is very effective to purify and crystallize reduced coenzyme $Q_{10}$ with simultaneous removal of impurities contained in the reaction mixture or extract containing reduced coenzyme $Q_{10}$ obtained in the conventional manner or produced by the reduction method to be described below or the like. This makes it possible to remove coexisting impurities, in particular analogous compounds having a similar structure and generally not always easy to remove (specifically, reduced coenzyme $Q_9$, reduced coenzyme $Q_8$, reduced coenzyme $Q_7$, etc.), into the mother liquor. Alcohols and/or ketones are also particularly effective solvents to remove said analogous compounds having a similar structure. Needless to say, it is possible to utilize the above purification and crystallization method as a method of recrystallizing reduced coenzyme $Q_{10}$ crystals.

The crystallization temperature of reduced coenzyme $Q_{10}$ may vary depending on the crystallization solvent species and/or crystallization method, hence cannot be absolutely specified. It is preferably not higher than 25° C., more preferably not higher than 20° C., further more preferably not higher than 15° C., particularly preferably not higher than 10° C. The lower limit is preferably the solidification temperature of the system. The crystallization is preferably carried out at 0 to 25° C. in general.

In the process of crystallization, the amount of crystals crystallizing out per unit time may be controlled to minimize the immixture of various impurities into the obtained reduced coenzyme $Q_{10}$, or to obtain a slurry with good characteristics. A preferred rate of crystallization per unit time is not higher than the rate of crystallization which causes crystallization of 50%, per unit time, of the whole amount of crystals to be obtained (50%/hour), more preferably not higher than the rate of crystallization which causes crystallization of 25%, per unit time, of the whole amount of crystals to be obtained (i.e. 25%/hour). The rate of cooling in the crystallization by cooling is preferably not higher than 40° C./hour, and more preferably not higher than 20° C./hour.

The crystallization of reduced coenzyme $Q_{10}$ is preferably carried out under forced flowing. For preventing the state of supersaturation from occurring and thereby allowing the nucleation and crystal growth to proceed smoothly and, furthermore, from the viewpoint of obtaining high-quality products, the flowing is generally brought about by a stirring power per unit volume of not weaker than about 0.01 kW/m$^3$, preferably not weaker than about 0.1 kW/m$^3$, and more preferably not weaker than about 0.3 kW/m$^3$. The forced flowing is generally provided by the turning of a stirring blade(s). However, the use of a stirring blade (s) is not always necessary if the above flowing can be otherwise obtained. For example, it is possible to utilize a method based on liquid circulation.

In carrying out the crystallization, seed crystals are preferably added so that the state of supersaturation may be prevented from occurring and the nucleation and crystal growth may be allowed to proceed smoothly.

The crystallization concentration may vary depending on the crystallization solvent species and/or the method of crystallization, hence cannot be absolutely specified. However, when expressed as the weight of reduced coenzyme $Q_{10}$ relative to the solvent weight at the time of completion of crystallization, it is preferably not more than 15 w/w %, more preferably not more than 13 w/w %, still more preferably not more than 10 w/w %. From the productivity viewpoint, the lower limit is preferably 1 w/w %, more preferably 2 w/w %. Generally, the crystallization can be favorably carried out at a concentration of 5 to 10 w/w %.

The thus-obtained crystals of reduced coenzyme $Q_{10}$ can be recovered as a wet product, for example, by such a solid-liquid separation technique as centrifugation, pressure filtration, or vacuum filtration, if necessary followed by cake washing. They can be recovered also as a dry product by further charging the wet product in a reduced pressure drier (vacuum drier) internally purged with an inert gas and drying the same under reduced pressure. The recovery in a dry form is preferred.

When reduced coenzyme $Q_{10}$ is crystallized in the above manner, the strong acid used in the step of crystallization may be removed after crystallization by employing, for example, the method comprising neutralizing the strong acid after crystallization with a base (e.g. alkali metal hydroxide such as sodium hydroxide), or the method comprising using a volatile strong acid, such as hydrogen chloride, as the strong acid, and evaporating the strong acid after crystallization.

In cases where the strong acid is neutralized with a base (e.g. alkali metal hydroxide such as sodium hydroxide; alkaline earth metal hydroxide such as magnesium hydroxide; alkali metal carbonate such as sodium carbonate; alkali metal hydrogencarbonate such as sodium hydrogencarbonate, etc) after crystallization, it is also preferable, for dissolving the salt formed as a byproduct upon neutralization in the mother liquor to thereby eliminate the salt, to cause water to coexist in the system for the dissolution and elimination of the salt on the occasion of crystal separation. Generally, this can be accomplished, for example, by carrying out the crystallization in the presence of water or adding water on the occasion of crystal separation.

The present invention is preferably practiced in a deoxygenated atmosphere, specifically in an inert gas atmosphere, under reduced pressure, and/or under boiling so that the oxidation inhibiting effect may further be enhanced. It is preferred that the invention be practiced at least in an inert atmosphere. The inert gas includes nitrogen gas, carbon dioxide gas, helium gas, argon gas, hydrogen gas and so on. Nitrogen gas is preferred, however.

A method of synthesizing reduced coenzyme $Q_{10}$ which is suited for use in the practice of the invention, namely a method of reducing oxidized coenzyme $Q_{10}$ to reduced coenzyme $Q_{10}$, is described in the following.

The reduced coenzyme $Q_{10}$ which is suited for use in the practice of the invention can be obtained in the conventional manner, for example by synthesis, fermentation, extraction from a natural source, etc, as mentioned above. Preferably, it can be obtained by reducing oxidized coenzyme $Q_{10}$, such as any of the existing high-purity grades of coenzyme $Q_{10}$, or a mixture of oxidized coenzyme $Q_{10}$ and reduced coenzyme $Q_{10}$ with a conventional reducing agent. First, a method of reducing oxidized coenzyme $Q_{10}$ is described.

Since reduced coenzyme $Q_{10}$ is readily oxidized by molecular oxygen to give oxidized coenzyme $Q_{10}$ as a byproduct, a solvent having high protective effect against oxidation is preferably used as the solvent in the step of reduction. Preferably used as such solvent among the solvents mentioned above is at least one species selected from among hydrocarbons, fatty acid esters, ethers, and nitriles. Hydrocarbons are most preferred.

In selecting the solvent to be used from among the solvents mentioned above, such properties as boiling point, viscosity, etc. (for example, the solvent should have a boiling point which allows appropriate warming for increasing the solubility and facilitates a solvent removal from wet masses by drying and solvent recovery from crystallization filtrates (about 30 to 150° C. at 1 atm), a melting point such that solidification hardly occurs in handling at room temperature as well as upon cooling to room temperature or below (not higher than about 20° C., preferably not higher than about 10° C., still more preferably not higher than about 0° C.), and a low viscosity (not higher than about 10 cp at 20° C.)) are preferably taken into consideration. From the industrial operation viewpoint, a solvent which is scarcely volatile at ordinary temperature is preferred; for example, generally, one having a boiling point of not lower than about 80° C. is preferred, and one having a boiling point of not lower than about 90° C. is more preferred.

Among the solvents mentioned above, as a solvent in the reduction reaction, a solvent having low miscibility with water is particularly preferably used. The solvent in the reduction reaction promotes purifying and obtaining a reduced coenzyme $Q_{10}$ efficiently, by extracting the reducing agent to be described below and/or impurities from the reducing agent and removing the same.

Reduced coenzyme $Q_{10}$, when in a dissolved state, tends to become more resistant to oxidation as the concentration thereof increases. Reduced coenzyme $Q_{10}$ is highly soluble in the solvents mentioned above and, in this respect, too, the above solvents are suitable for the protection from oxidation. The concentration of reduced coenzyme $Q_{10}$ which is preferred from the viewpoint of protection thereof from oxidation may vary depending on the solvent species, among others, hence cannot be absolutely specified. Generally, however, the concentration of reduced coenzyme $Q_{10}$ in the above solvents is generally not lower than 1 w/w %, preferably not lower than 2 w/w %. The upper limit is not particularly restricted but, from the practical operability viewpoint, it is 400 w/w %, preferably 200 w/w %, more preferably 100 w/w %, still more preferably 50 w/w %.

Thus, by using the above solvents, an undesirable oxygen-involving side reaction is minimized via the step of reduction.

The reduction reaction can be carried out, in the above solvent, using, as a reducing agent, a metal hydride compound, iron (metallic iron or iron in a salt form), zinc (metallic zinc), diothionous acid or a salt thereof, or an ascorbic acid or a related compound thereof, for instance.

The metal hydride compound is not particularly restricted but includes, among others, sodium borohydride, lithium aluminum hydride, etc. The amount to be used of the metal hydride compound may vary depending on the species thereof, hence cannot be absolutely specified. Generally, however, the reduction can be favorably carried out by using it in an amount of 1 to 3 times the theoretical hydrogen equivalent.

The reduction using iron or zinc is generally carried out using an acid. The acid is not particularly restricted but includes, among others, fatty acids such as acetic acid, sulfonic acids such as methanesulfonic acid, inorganic acids such as hydrochloric acid and sulfuric acid, etc. Inorganic acids are preferred, and sulfuric acid is more preferred.

The amount of iron to be used is not particularly restricted but, for example, an amount of about ⅕ by weight or larger based on the charged weight of oxidized coenzyme $Q_{10}$ is appropriate for carrying out the reaction. The upper limit is not particularly restricted but, from the economical viewpoint, it is about twice the weight of the above charged weight. Iron may be used not only in the form of metallic iron but also in the form of a salt, for example iron(II) sulfate, etc.

The amount of zinc to be used is not particularly restricted but, for example, an amount of about 1/10 by weight or larger based on the charged weight of oxidized coenzyme $Q_{10}$ is appropriate for carrying out the reaction. The upper limit is not particularly restricted but, from the economic viewpoint, it is about twice the weight of the above charged weight.

The dithionous acid or a salt thereof is not particularly restricted but a salt form of dithionous acid is generally used. The salt of dithionous acid is not particularly restricted but includes, as preferred species, alkali metal salts, alkaline earth metal salts, ammonium salt and the like. Alkali metal salts such as the lithium salt, sodium salt, and potassium salt are more preferred, and the sodium salt is most preferred.

The amount to be used of the dithionous acid or salt is not particularly restricted but it is generally not smaller than about 1/5 by weight, preferably not smaller than about 2/5 by weight, and more preferably not smaller than about 3/5 by weight, based on the charged weight of oxidized coenzyme $Q_{10}$. Larger amounts may be used without causing any particularly trouble. In consideration of economical disadvantages, however, the amount to be used is not larger than about twice the weight of the above-mentioned charged weight, preferably not larger than the charged weight. Generally, the reaction can be favorably carried out with using an amount within the range of about 2/5 by weight of the above-mentioned charge to a weight roughly equal to that of the charged weight.

The ascorbic acid or related compounds thereof are not particularly restricted, and include, for example, not only ascorbic acid, but also rhamno-ascorbic acid, arabo-ascorbic acid, gluco-ascorbic acid, fuco-ascorbic acid, glucohepto-ascorbic acid, xylo-ascorbic acid, galacto-ascorbic acid, gulo-ascorbic acid, allo-ascorbic acid, erythro-ascorbic acid, 6-desoxyascorbic acid, and the like ascorbic acid-related compounds thereof, and may be ester forms or salts of these. Furthermore, these may be L-form, D-form or racemic form. Specifically, there may be mentioned, for example, L-ascorbic acid, L-ascorbyl palmitate, L-ascorbyl stearate, D-arabo-ascorbic acid, etc. In producing the reduced coenzyme $Q_{10}$, any of the above-mentioned ascorbic acid or related compounds thereof may be suitably used. However, the water-soluble ones are suitably used in particular among the above-mentioned ascorbic acid or related compounds thereof in view of separatability with the generated reduced coenzyme $Q_{10}$, etc. And most preferred is a free form of L-ascorbic acid, D-arabo-ascorbic acid, and the like in view of the ready availability, price, etc.

The amount to be used of the ascorbic acid or related compounds thereof mentioned above is not particularly restricted but may be an amount effective in converting oxidized coenzyme $Q_{10}$ to reduced coenzyme $Q_{10}$. Generally it is not smaller than 1 mole, preferably not smaller than 1.2 moles, per mole of oxidized coenzyme $Q_{10}$. The upper limit is not particularly restricted but, from the economical viewpoint, it is generally 10 moles, preferably 5 moles, and more preferably 3 moles, per mole of the oxidized coenzyme $Q_{10}$.

Among the reducing agent species mentioned above, zinc, dithionous acid and salts thereof, and ascorbic acid or related compounds thereof are preferred from the viewpoint of reducing ability, yield, quality, etc, and, in particular, dithionous acid or salts thereof (specifically dithionous acid salts) and ascorbic acid or related compounds thereof are preferred.

In carrying out the reduction reaction, an alcohol and/or water are/is suitably used, as mentioned above. Water is preferred in particular when iron, zinc, or dithionous acid or a salt thereof is used as the reducing agent. When a metal hydride compound or an ascorbic acid or a related compound thereof is used as the reducing agent, an alcohol can be used in combination. The combined use of water and an alcohol exhibits the characteristics of both water and the alcohol and contributes to improvements in reaction rate and yield, etc.

In the following, a preferred method of reduction is described in detail.

The reduction using dithionous acid or a salt thereof is preferably carried out in a mixed solvent system composed of water with at least one organic solvent among the above-mentioned hydrocarbons, fatty acid esters, ethers, and nitriles (among these organic solvents, preferred are hydrocarbons, more preferred aliphatic hydrocarbons, further more preferred heptanes, particularly preferred heptane). On that occasion, the reaction is preferably carried out generally at a pH of not higher than 7, preferably at pH 3 to 7, more preferably at pH 3 to 6, from the viewpoint of yield, etc. The pH can be adjusted using an acid (e.g. a mineral acid such as hydrochloric acid or sulfuric acid) or a base (e.g. an alkali metal hydroxide such as sodium hydroxide).

In the reduction using dithionous acid or a salt thereof, the amount of water is not particularly restricted but may be an appropriate amount of water such that an amount of the reducing agent, namely dithionous acid or a salt thereof, can be dissolved therein. Thus, for example, it is advisable that the amount of the dithionous acid or a salt be adjusted generally to not more than 30 w/w %, and preferably not more than 20 w/w %, relative to the weight of water. From the productivity viewpoint, etc, it is advisable that the amount be adjusted generally to not less than 1 w/w %, preferably not less than 5 w/w %, and more preferably not less than 10 w/w %.

The reduction using the ascorbic acid or a related compound thereof mentioned above can be carried out using a solvent especially highly miscible with water as selected from among the above-mentioned hydrocarbons, fatty acid esters, ethers, and nitrites, in particular ethers and nitriles, which are highly miscible with water, and more specifically tetrahydrofuran, dioxane, acetonitrile or the like. It is particularly preferred to use the above-mentioned alcohols and/or ketones (preferably alcohols and/or ketones, which are highly miscible with water (in particular, monohydric or dihydric alcohols (preferably monohydric ones) having 1 to 5 carbon atoms, preferably 1 to 4 carbon atoms, more preferably 1 to 3 carbon atoms, and/or, ketones such as acetone, methyl ethyl ketone or the like)). Namely, in the reduction using the ascorbic acid or a related compound thereof, it is preferable to use alcohols and/or water-soluble organic solvents. Furthermore, from the viewpoint of reaction promotion (e.g. reaction temperature lowering or reaction time shortening) in the production of reduced coenzyme $Q_{10}$, it is also possible to carry out the reduction in the presence of an additive having a reaction promoting effect, such as a basic substance or a hydrogensulfite.

The basic compound is not particularly restricted but may be either an inorganic compound or an organic compound. The inorganic compound is not particularly restricted but includes, among others, the hydroxides, carbonates, and hydrogencarbonates of metals (preferably alkali metals, alkaline earth metals, and the like), ammonia, etc. As typical examples thereof, there may be mentioned alkali metal hydroxides such as sodium hydroxide, alkali metal carbonates such as sodium carbonate, alkali metal hydrogencarbonates such as sodium hydrogencarbonate, alkaline earth metal carbonates such as magnesium carbonate, etc. The organic compound is not particularly restricted but includes, among others, amines such as triethylamine, etc. Among the basic substances specifically mentioned above, weakly basic substances (weak bases or weak alkalis) such as the carbonates and hydrogencarbonates of metals (preferably alkali metals, alkaline earth metals, etc.), ammonia, and like inorganic compounds; amines such as triethylamine, and like organic compounds are particularly preferably used. More preferred are the weakly basic inorganic compounds mentioned above.

Preferred as the hydrogensulfite are, for example, alkali metal hydrogensulfites such as sodium hydrogensulfite, etc.

The amount of the additive mentioned above is not particularly restricted but may be such that the reaction promoting effect of the additive can be produced to a desired extent (effective amount). From the economical viewpoint, however, the amount is generally not more than 20 moles, preferably not more than 10 moles, more preferably not more than 5 moles, and particularly preferably not more than 2 moles, per mole of the ascorbic acid or a related compound thereof. The lower limit is not particularly restricted but, generally, it is 0.01 moles, preferably 0.05 moles, more preferably 0.1 moles, and particularly preferably 0.2 moles, per mole of the ascorbic acid or a related compound thereof.

In the practice of the invention, the reduction reaction is preferably carried out under forced flowing. The power required for stirring to cause such flowing per unit volume is generally not less than about 0.01 kW/m$^3$, preferably not less than about 0.1 kW/m$^3$, and more preferably not less than about 0.3 kW/m$^3$. The above forced flowing is generally caused by the turning of a stirring blade(s). The use of a stirring blade(s) is not always necessary if the above flowing can be otherwise obtained. For example a method based on liquid circulation may be utilized.

The reduction temperature may vary depending on the reducing agent species and/or amount, hence cannot be absolutely specified. In the reduction using dithionous acid or a salt thereof, for instance, the reduction is generally carried out at 100° C. or below, preferably at 80° C. or below, more preferably at 60° C. or below. The lower limit is the solidification temperature of the system. Thus, the reduction can be favorably carried out generally at about 0 to 100° C., preferably at about 0 to 80° C., more preferably at about 0 to 60° C. In the reduction using an ascorbic acid or a related compound thereof, the reduction is carried out generally at 30° C. or higher, preferably at 40° C. or higher, more preferably at 50° C. or higher. The upper limit is the boiling point of the system. Thus, the reduction can be favorably carried out generally at about 30 to 150° C., preferably about 40 to 120° C., more preferably at about 50 to 100° C.

The reaction concentration is not particularly restricted but the weight of oxidized coenzyme $Q_{10}$ relative to the solvent weight is generally not less than about 1 w/w %, preferably not less than 3 w/w %, more preferably not less than 10 w/w %, and still more preferably not less than 15 w/w %. The upper limit is not particularly restricted but generally is not higher than 60 w/w %, preferably not higher than 50 w/w %, more preferably not higher than 40 w/w %, and still more preferably not higher than 30 w/w %. Thus, generally, the reaction can be favorably carried out at a reaction concentration of about 1 to 60 w/w %, preferably about 3 to 50 w/w %, and more preferably about 10 to 40 w/w %.

Generally, the reduction reaction can be driven to completion within 48 hours, preferably within 24 hours, more preferably within 10 hours, and still more preferably within 5 hours.

An organic phase containing the product reduced coenzyme $Q_{10}$ is recovered from the thus-obtained reduction reaction mixture and, if necessary (preferably), the organic phase is further washed repeatedly using water, brine, or the like to achieve complete contaminant elimination. When the dithionous acid or a salt thereof mentioned above, in particular, is used as the reducing agent, it is desirable to repeat washing with water so that contaminants derived from the dithionous acid or a salt thereof may be removed completely and/or the pH of the aqueous phase may be stabilized. Additionally, in order to obtain desired solution containing reduced coenzyme $Q_{10}$, the reduction reaction mixture may be subjected to concentration and/or solvent substitution, if necessary.

It is exceedingly preferable to carry out the reduction reaction and after-treatment in a deoxygenated atmosphere. Surprisingly, it was found that, in the reduction reaction using dithionous acid or a salt thereof, in particular, such atmosphere greatly contributes to an improvement in reduction reaction yield and a decrease of the reducing agent. The deoxygenated atmosphere can be attained by substitution with an inert gas, pressure reduction, boiling, or a combination of these. It is preferable to carry out at least the substitution with an inert gas, namely to use an inert gas atmosphere. As the inert gas, there may be mentioned, for example, nitrogen gas, helium gas, argon gas, hydrogen gas, carbon dioxide gas, etc. Nitrogen gas is preferred, however.

In accordance with the present invention described hereinabove, the undesirable oxygen-involving side reaction in the step of crystallization of reduced coenzyme $Q_{10}$ is minimized through the use of a strong acid. Further, reduced coenzyme $Q_{10}$ can be protected against oxidation by molecular oxygen and thus stabilized by handling reduced coenzyme $Q_{10}$ in the presence of a strong acid, so that such operations as extraction, washing with water, concentration and column chromatography can be carried out successfully.

The reduced coenzyme $Q_{10}$ crystals obtained by the crystallization method of the invention are of very high quality and expected to have a reduced coenzyme $Q_{10}$/oxidized coenzyme $Q_{10}$ weight ratio of not less than 98/2, preferably not less than 99/1.

BEST MODE FOR CARRYING OUT THE INVENTION

The following examples illustrate the present invention in further detail. These examples are, however, by no means limitative of the scope of the present invention. In the examples, the purity of reduced coenzyme $Q_{10}$ and the reduced coenzyme $Q_{10}$/oxidized coenzyme $Q_{10}$ weight ratio were determined by the HPLC analysis specified below. The reduced coenzyme $Q_{10}$ purity values as determined, however, are by no means indicative of the limit purity value attainable in accordance with the present invention. Likewise, the reduced coenzyme $Q_{10}$/oxidized coenzyme $Q_{10}$ weight ratio values obtained never indicate the upper limit to that ratio.

(HPLC Conditions)

Column: SYMMETRY C18 (product of Waters), 250 mm (in length), 4.6 mm (in inside diameter); mobile phase: $C_2H_5OH:CH_3OH=4:3$ (v/v); detection wavelength: 210 nm; flow rate: 1 ml/min; retention time of reduced coenzyme $Q_{10}$: 9.1 min; retention time of oxidized coenzyme $Q_{10}$: 13.3 min.

EXAMPLE 1

Ten grams of oxidized coenzyme $Q_{10}$ (purity 99.4%) was dissolved in 100 g of heptane at 25° C. While stirring (power required for stirring 0.3 kW/m$^3$), an aqueous solution prepared by adding 10 g of sodium dithionite (at least 75% pure), as the reducing agent, to 100 ml of water for dissolution thereof was gradually added and the reduction reaction was carried out at 25° C. After 2 hours, the aqueous phase was removed from the reaction mixture, and the heptane phase was washed 6 times with a washing liquid prepared by adding 2 g of 0.1 N hydrochloric acid to 100 g of saturated brine. All the above operations were carried out in a nitrogen atmosphere. A 1 w/w % ethanol solution of reduced coenzyme $Q_{10}$ was prepared by subjecting the above heptane solution to solvent substitution under reduced pressure.

The ethanol solution was divided into 100-g portions, and the strong acids specified in Table 1 were added to the respective portions in an amount corresponding to 100 mmol/kg of ethanol and to 1000 mol % relative to reduced coenzyme $Q_{10}$, and the resulting mixtures were stirred in the air (in the case of hydrogen chloride, this was added in the form of 12 N hydrochloric acid). The reduced coenzyme $Q_{10}$/oxidized coenzyme $Q_{10}$ weight ratios in the ethanol solutions as determined after 24 hours are shown in Table 1. For comparison, the results obtained by adding acetic acid (100 mmol/kg of ethanol) and without adding any acid are also shown.

TABLE 1

| | R |
|---|---|
| Hydrogen chloride | 98.7/1.3 |
| Sulfuric acid | 98.8/1.2 |
| Methanesulfonic acid | 97.8/2.2 |
| Acetic acid | 59.0/41.0 |
| Control (no acid addition) | 54.0/46.0 |

R: Reduced coenzyme $Q_{10}$/oxidized coenzyme $Q_{10}$ weight ratio

EXAMPLE 2

A heptane solution of reduced coenzyme $Q_{10}$ was prepared in the same manner as in Example 1. A 1 w/w % dimethylformamide solution of reduced coenzyme $Q_{10}$ was prepared by subjecting the heptane solution to solvent substitution under reduced pressure. The dimethylformamide solution was divided into 100-g portions, and the strong acids specified in Table 2 were added to the respective portions in an amount corresponding to 100 mmol/kg of dimethylformamide and to 1000 mol % relative to reduced coenzyme $Q_{10}$, and the resulting mixtures were stirred in the air (in the case of hydrogen chloride, this was added in the form of 12 N hydrochloric acid). The reduced coenzyme $Q_{10}$/oxidized coenzyme $Q_{10}$ weight ratios in the dimethylformamide solutions as determined after 24 hours are shown in Table 2. For comparison, the results obtained by adding acetic acid (100 mmol/kg of dimethylformamide) and without adding any acid are also shown.

TABLE 2

| | R |
|---|---|
| Hydrogen chloride | 99.2/0.8 |
| Sulfuric acid | 99.4/0.6 |
| Methanesulfonic acid | 99.0/1.0 |
| Acetic acid | 65.0/35.0 |
| Control (no acid addition) | 75.1/24.9 |

R: Reduced coenzyme $Q_{10}$/oxidized coenzyme $Q_{10}$ weight ratio

EXAMPLE 3

To 100 g of a 1 w/w % ethanol solution of reduced coenzyme $Q_{10}$ obtained in the same manner as in Example 1, 12 N hydrochloric acid was added in an amount corresponding, as hydrogen chloride, to 100 mmol/kg (relative to ethanol) and to 1000 mol % relative to reduced coenzyme $Q_{10}$, and the mixture was stirred in a nitrogen atmosphere. The reduced coenzyme $Q_{10}$/oxidized coenzyme $Q_{10}$ weight ratio in the ethanol solution after 24 hours was 99.4/0.6.

EXAMPLE 4

To 100 g of a 1 w/w % ethanol solution of reduced coenzyme $Q_{10}$ obtained in the same manner as in Example 1, 1 g of 1 N hydrochloric acid was added (corresponding, as hydrogen chloride, to 10 mmol/kg of ethanol and to 100 mol % relative to reduced coenzyme $Q_{10}$), and the mixture was stirred in the air. The reduced coenzyme $Q_{10}$/oxidized coenzyme $Q_{10}$ weight ratio in the ethanol solution after 24 hours was 98.7/1.3.

EXAMPLE 5

To 100 g of a 1 w/w % ethanol solution of reduced coenzyme $Q_{10}$ obtained in the same manner as in Example 1, 1 g of 0.1 N hydrochloric acid was added (corresponding, as hydrogen chloride, to 1 mmol/kg of ethanol and to 10 mol % relative to reduced coenzyme $Q_{10}$), and the mixture was stirred in the air. The reduced coenzyme $Q_{10}$/oxidized coenzyme $Q_{10}$ weight ratio in the ethanol solution after 24 hours was 98.7/1.3.

EXAMPLE 6

To 100 g of a 1 w/w % ethanol solution of reduced coenzyme $Q_{10}$ obtained in the same manner as in Example 1, 1 g of 0.01 N hydrochloric acid was added (corresponding, as hydrogen chloride, to 0.1 mmol/kg of ethanol and to 1 mol % relative to reduced coenzyme $Q_{10}$), and the mixture was stirred in the air. The reduced coenzyme $Q_{10}$/oxidized coenzyme $Q_{10}$ weight ratio in the ethanol solution after 24 hours was 98.5/1.5.

EXAMPLE 7

A reduced coenzyme $Q_{10}$-containing heptane phase was obtained in the same manner as in Example 1. A 7 w/w % ethanol solution of reduced coenzyme $Q_{10}$ was prepared by subjecting the heptane solution to solvent substitution under reduced pressure. To the ethanol solution, 1.4 g of 1 N hydrochloric acid was added (corresponding, as hydrogen chloride, to 10 mmol/kg of ethanol and to 12 mol % relative to reduced coenzyme $Q_{10}$), and the mixture was cooled to 2° C. while stirring (power required for stirring 0.3 kW/m$^3$) in the air, whereby a white slurry was obtained. The slurry obtained was filtered under reduced pressure, and the wet crystals were washed in sequence with cold ethanol, cold water and cold ethanol (the cold solvents used for washing having a temperature of 2° C.). The wet crystals were then dried under reduced pressure (20 to 40° C., 1 to 30 mmHg) to give 9.5 g of dry white crystals (isolated product yield 95 mol %). The reduced coenzyme $Q_{10}$/oxidized coenzyme $Q_{10}$ weight ratio of the crystals obtained was 99.1/0.9, and the purity of the reduced coenzyme $Q_{10}$ was 98.9%.

EXAMPLE 8

The procedure of Example 7 was followed exactly in the same manner except that 1.4 g of 0.01 N hydrochloric acid (corresponding, as hydrogen chloride, to 0.1 mmol/kg of ethanol and to 0.1 mol % relative to reduced coenzyme $Q_{10}$) was added in lieu of 1 N hydrochloric acid on the occasion of crystallization, to give 9.5 g of dry white crystals (isolated product yield 95 mol %). The reduced coenzyme $Q_{10}$/oxidized coenzyme $Q_{10}$ weight ratio of the crystals obtained was 99.0/1.0, and the purity of the reduced coenzyme $Q_{10}$ was 98.9%.

EXAMPLE 9

The procedure of Example 7 was followed exactly in the same manner except that the crystallization was carried out in a nitrogen atmosphere, to give 9.5 g of dry white crystals (isolated product yield 95 mol %). The reduced coenzyme $Q_{10}$/oxidized coenzyme $Q_{10}$ weight ratio of the crystals obtained was 99.5/0.5, and the purity of the reduced coenzyme $Q_{10}$ was 99.3%.

EXAMPLE 10

A white slurry containing the reduced coenzyme was obtained in the same manner as in Example 9. The slurry obtained was neutralized with a 5% sodium hydrogencarbonate solution and further filtered under reduced pressure. The wet crystals were washed in sequence with cold ethanol, cold water and cold ethanol (the cold solvents used for washing having a temperature of 2° C.). The wet crystals after washing were dried under reduced pressure (20 to 40° C., 1 to 30 mmHg) to give 9.5 g of dry white crystals (isolated product yield 95 mol %). The reduced coenzyme $Q_{10}$/oxidized coenzyme $Q_{10}$ weight ratio of the crystals obtained was 99.5/0.5, and the purity of the reduced coenzyme $Q_{10}$ was 99.3%.

COMPARATIVE EXAMPLE 1

The procedure of Example 7 was followed exactly in the same manner except that 1.4 g of water was added in lieu of 1 N hydrochloric acid on the occasion of crystallization, to give 9.5 g of dry white crystals (isolated product yield 95 mol %). The reduced coenzyme $Q_{10}$/oxidized coenzyme $Q_{10}$ weight ratio of the crystals obtained was 97.4/2.6, and the purity of the reduced coenzyme $Q_{10}$ was 97.2%.

EXAMPLE 11

A reduced coenzyme $Q_{10}$-containing heptane phase was obtained in the same manner as in Example 1. A 7 w/w % solution of reduced coenzyme $Q_{10}$ was prepared by subjecting the heptane solution to solvent substitution under reduced pressure and using ethanol containing 5% of water. To the ethanol solution, 1.4 g of 1 N hydrochloric acid was added (corresponding, as hydrogen chloride, to 10 mmol/kg of ethanol and to 12 mol % relative to reduced coenzyme $Q_{10}$), and the mixture was cooled to 2° C. while stirring (power required for stirring 0.3 kW/m$^3$) in the air, whereby a white slurry was obtained. The slurry obtained was filtered under reduced pressure (better filterability as compared with Example 7), and the wet crystals were washed in sequence with cold ethanol, cold water and cold ethanol (the cold solvents used for washing having a temperature of 2° C.). The wet crystals were then dried under reduced pressure (20 to 40° C., 1 to 30 mmHg) to give 9.7 g of dry white crystals (isolated product yield 97 mol %). The reduced coenzyme $Q_{10}$/oxidized coenzyme $Q_{10}$ weight ratio of the crystals obtained was 99.1/0.9, and the purity of the reduced coenzyme $Q_{10}$ was 98.9%.

EXAMPLE 12

The procedure of Example 11 was followed exactly in the same manner except that the crystallization was carried out in a nitrogen atmosphere, to give 9.7 g of dry white crystals (isolated product yield 97 mol %). The reduced coenzyme $Q_{10}$/oxidized coenzyme $Q_{10}$ weight ratio of the crystals obtained was 99.5/0.5, and the purity of the reduced coenzyme $Q_{10}$ was 99.3%.

EXAMPLE 13

A reduced coenzyme $Q_{10}$-containing heptane phase (containing 1.00% of reduced coenzyme $Q_9$, 0.30% of reduced coenzyme $Q_8$ and 0.04% of reduced coenzyme $Q_7$) was obtained in the same manner as in Example 1 except that the oxidized coenzyme $Q_{10}$ had a purity of 98.4% (containing 1.00% of oxidized coenzyme $Q_9$, 0.30% of oxidized coenzyme $Q_8$ and 0.04% of oxidized coenzyme $Q_7$). This heptane solution was subjected to solvent substitution under reduced pressure to give a 7 w/w % solution of reduced coenzyme $Q_{10}$ in ethanol. To this ethanol solution was added 1.4 g of 1 N hydrochloric acid (corresponding, as hydrogen chloride, to 10 mmol/kg of ethanol and to 12 mol % relative to reduced coenzyme $Q_{10}$), and the mixture was cooled to 2° C. while stirring (power required for stirring 0.3 kW/m$^3$) in the air, whereby a white slurry was obtained. The slurry obtained was filtered under reduced pressure, and the wet crystals were washed in sequence with cold ethanol, cold water and cold ethanol (the cold solvents used for washing having a temperature of 2° C.). The wet crystals were then dried under reduced pressure (20 to 40° C., 1 to 30 mmHg) to give 9.5 g of dry white crystals (containing 0.52% of reduced coenzyme $Q_9$, percentage of elimination 48%; neither reduced coenzyme $Q_8$ nor reduced coenzyme $Q_7$ detected) (isolated product yield 95mol %) The reduced coenzyme $Q_{10}$/oxidized coenzyme $Q_{10}$ weight ratio of the crystals obtained was 99.1/0.9, and the purity of the reduced coenzyme $Q_{10}$ was 98.9%.

EXAMPLE 14

Ten grams of oxidized coenzyme $Q_{10}$, 6 g of L-ascorbic acid and 3 g of sodium hydrogencarbonate were added to 100 g of ethanol, and the reduction reaction was carried out with stirring at 78° C. After 3 hours, the reaction mixture was cooled to 50° C., 100 g of heptane and 100 g of deaerated water were added to the mixture, and the whole mixture was cooled to 25° C. The aqueous layer was removed, the heptane phase was further washed 6 times with 100 g of deaerated saturated brine. The heptane solution was subjected to solvent substitution under reduced pressure to give a 7 w/w % solution of reduced coenzyme $Q_{10}$ in ethanol. To this ethanol solution, 1.4 g of 1 N hydrochloric acid was added (corresponding, as hydrogen chloride, to 10 mmol/kg of ethanol and to 12 mol % relative to reduced coenzyme $Q_{10}$), and the mixture was cooled to 2° C. while stirring (power required for stirring 0.3 kW/m$^3$) in the air, whereby a white slurry was obtained. The slurry obtained was filtered under reduced pressure, and the wet crystals were washed in sequence with cold ethanol, cold water and cold ethanol (the cold solvents used for washing having a temperature of 2° C.). The wet crystals were then dried under reduced pressure (20 to 40° C., 1 to 30 mmHg) to give 9.5 g of dry white crystals (isolated product yield 95 mol %). The reduced coenzyme $Q_{10}$/oxidized coenzyme $Q_{10}$ weight ratio of the crystals obtained was 99.1/0.9, and the purity of the reduced coenzyme $Q_{10}$ was 98.9%.

EXAMPLE 15

A heptane solution of reduced coenzyme $Q_{10}$ was obtained in the same manner as in Example 1. A 7 w/w % acetone solution of reduced coenzyme $Q_{10}$ was prepared by subjecting the heptane solution to solvent substitution under reduced pressure. To the acetone solution, 1.4 g of 1 N hydrochloric acid was added (corresponding, as hydrogen chloride, to 10 mmol/kg of acetone and to 12 mol % relative to reduced coenzyme $Q_{10}$), and the mixture was cooled to 2° C. while stirring (power required for stirring 0.3 kW/m$^3$) in the air, whereby a white slurry was obtained. The slurry obtained was filtered under reduced pressure, and the wet crystals were washed in sequence with cold acetone, cold water and cold acetone (the cold solvents used for washing having a temperature of 2° C.). The wet crystals were then dried under reduced pressure (20 to 40° C., 1 to 30 mmHg) to give 9.4 g of dry white crystals (isolated product yield 94 mol %). The reduced coenzyme $Q_{10}$/oxidized coenzyme $Q_{10}$ weight ratio of the crystals obtained was 99.3/0.7, and the purity of the reduced coenzyme $Q_{10}$ was 99.0%.

COMPARATIVE EXAMPLE 2

The procedure of Example 11 was carried out exactly in the same manner except that 1.4 g of water was added in lieu of 1 N hydrochloric acid on the occasion of crystallization, whereby 9.7 g of dry white crystals (isolated product yield 97 mol %) was obtained. The reduced coenzyme $Q_{10}$/oxidized-coenzyme $Q_{10}$ weight ratio of the crystals obtained was 97.4/2.6, and the purity of the reduced coenzyme $Q_{10}$ was 97.2%.

REFERENCE EXAMPLE 1

One gram of reduced coenzyme $Q_{10}$ (reduced coenzyme $Q_{10}$/oxidized coenzyme $Q_{10}$ weight ratio 99.6/0.4) was dissolved in 20 g of each of the solvents specified in Table 3 at 25° C. After 24 hours of stirring in the air at 25° C., the reduced coenzyme $Q_{10}$/oxidized coenzyme $Q_{10}$ weight ratio in each solution was determined. The results thus obtained are shown in Table 3.

TABLE 3

| Solvent | R |
| --- | --- |
| Heptane | 99.1/0.9 |
| Hexane | 98.7/1.3 |
| Toluene | 98.8/1.2 |
| Chloroform | 98.9/1.1 |
| Ethyl acetate | 98.9/1.1 |
| Methyl tert-butyl ether | 98.6/1.4 |
| Tetrahydrofuran | 98.5/1.5 |

R: Reduced coenzyme $Q_{10}$/oxidized coenzyme $Q_{10}$ weight ratio

REFERENCE EXAMPLE 2

One gram of reduced coenzyme $Q_{10}$ (reduced coenzyme $Q_{10}$/oxidized coenzyme $Q_{10}$ weight ratio 99.6/0.4) was dissolved in 100 g of each of the solvents specified in Table 4 at 35° C. After 24 hours of stirring in the air at 35° C., the reduced coenzyme $Q_{10}$/oxidized coenzyme $Q_{10}$ weight ratio in each solution was determined. The results thus obtained are shown in Table 4.

TABLE 4

| Solvent | R |
| --- | --- |
| Heptane | 96.7/3.3 |
| Ethyl acetate | 96.4/3.6 |
| Acetonitrile | 96.0/4.0 |

R: Reduced coenzyme $Q_{10}$/oxidized coenzyme $Q_{10}$ weight ratio

INDUSTRIAL APPLICABILITY

The invention, which has the constitution described above, is a method suited for commercial scale production and can give high-quality reduced coenzyme $Q_{10}$ in a convenient and efficient manner.

The invention claimed is:

1. A method of stabilizing reduced coenzyme $Q_{10}$ which comprises contacting reduced coenzyme $Q_{10}$ with a solvent containing a strong acid to thereby protect reduced coenzyme $Q_{10}$ against oxidation by molecular oxygen,
    wherein the strong acid shows a pKa value of not more than 2.5 in aqueous solution, and
    wherein reduced coenzyme $Q_{10}$ is contacted with said solvent at a moment of at least one operation selected from the group consisting of extraction, concentration and column chromatography.
2. The method according to claim 1,
    wherein the strong acid is an inorganic acid.
3. The method according to claim 1,
    wherein the amount of strong acid to be used is not less than 0.1 mol % of reduced coenzyme $Q_{10}$.
4. The method according to claim 1,
    wherein the concentration of the strong acid in the solvent as expressed in terms of the molar quantity of the strong acid relative to the solvent weight is not less than 0.1 mmol/kg.
5. The method according to claim 1,
    wherein the solvent comprises at least one species selected from the group consisting of hydrocarbons, fatty acid esters, ethers, alcohols, fatty acids, ketones, nitrogen compounds, sulfur compounds, and water.
6. The method according to claim 5,
    wherein the solvent comprises at least one species selected from the group consisting of alcohols, ketones, nitrogen compounds, and water.
7. The method according to claim 6,
    wherein the solvent comprises at least one species selected from the group, consisting of alcohols containing 1 to 3 carbon atoms, acetone, acetonitrile, and water.
8. The method according to claim 7,
    wherein the solvent is ethanol or a mixed solvent composed of ethanol and water.
9. The method according to claim 8,
    wherein the proportion of ethanol in the mixed solvent composed of ethanol and water is 90 to 99.5 w/w %.
10. The method according to claim 1,
    wherein the concentration of reduced coenzyme $Q_{10}$ in the solvent is not less than 1 w/w %.

11. The method according to claim 1,
wherein reduced coenzyme $Q_{10}$ is handled in a deoxygenated atmosphere.

12. A method of crystallizing reduced coenzyme $Q_{10}$ which comprises crystallizing reduced coenzyme $Q_{10}$ in a solvent containing a strong acid,
wherein the strong acid shows a pKa value of not less than 2.5 in aqueous solution.

13. The method according to claim 12,
wherein the strong acid is an inorganic acid.

14. The method according to claim 1,
wherein the amount of strong acid to be used is not less than 0.1 mol % per mole of reduced coenzyme $Q_{10}$.

15. The method according to claim 12,
wherein the concentration of the strong acid in the solvent as expressed in terms of the molar quantity of the strong acid relative to the solvent weight is not less than 0.1 mmol/kg.

16. The method according to claim 12,
wherein the solvent comprises at least one species selected from the group consisting of hydrocarbons, fatty acid esters, ethers, alcohols, fatty acids, ketones, nitrogen compounds, sulfur compounds, and water.

17. The method according to claim 16,
wherein the solvent comprises at least one species selected from the group consisting of alcohols, ketones, nitrogen compounds, and water.

18. The method according to claim 17,
wherein the solvent comprises at least one species selected from the group consisting of alcohols containing 1 to 3 carbon atoms, acetone, acetonitrile, and water.

19. The method according to claim 18,
wherein the solvent is ethanol or a mixed solvent composed of ethanol and water.

20. The method according to claim 19,
wherein the proportion of ethanol in the mixed solvent composed of ethanol and water is 90 to 99.5 w/w %.

21. The method according to claim 12,
wherein an impurity or impurities are eliminated into mother liquor.

22. The method according to claim 21,
wherein the impurity to be eliminated comprises at least one species selected from the group consisting of reduced coenzyme $Q_9$, reduced coenzyme $Q_8$, and reduced coenzyme $Q_7$.

23. The method according to claim 12,
wherein the crystallization concentration as expressed in terms of the weight of reduced coenzyme $Q_{10}$ relative to the weight of the crystallization solvent at the time of completion of crystallization is not less than 1 w/w %.

24. The method according to claim 23, wherein the crystallization concentration as expressed in terms of the weight of reduced coenzyme $Q_{10}$ relative to the weight of the crystallization solvent at the time of completion of crystallization is 5 to 10 w/w %.

25. The method according to claim 12,
wherein a volatile strong acid is used as the strong acid and the volatile strong acid is evaporated after crystallization of reduced coenzyme $Q_{10}$.

26. The method according to claim 12,
wherein the strong acid is neutralized with a base after crystallization.

27. The method according to claim 26,
wherein the base is an alkali metal hydroxide, an alkaline earth metal hydroxide, an alkali metal carbonate, or an alkali metal hydrogencarbonate.

28. The method according to claim 12,
wherein the crystallization process is carried out in a deoxygenated atmosphere.

29. The method accordingly to claim 26,
wherein separation of crystals of reduced coenzyme $Q_{10}$ is carried out in the presence of water to thereby dissolve and eliminate the salt formed as a by-product upon neutralization in mother liquor.

* * * * *